US00PP15739P2

(12) United States Plant Patent
Lim et al.

(10) Patent No.: US PP15,739 P2
(45) Date of Patent: Apr. 26, 2005

(54) SHRUB ROSE PLANT NAMED 'BAISIST'

(50) Latin Name: *Rosa hybrida*
Varietal Denomination: BAIsist

(75) Inventors: Peter P. Lim, Yamhill, OR (US); Jerry Twomey, Leucadia, CA (US)

(73) Assignee: Bailey Nurseries, Inc., St. Paul, MN (US)

( * ) Notice: Subject to any disclaimer, the term of this patent is extended or adjusted under 35 U.S.C. 154(b) by 39 days.

(21) Appl. No.: 10/811,994

(22) Filed: Mar. 30, 2004

(51) Int. Cl.[7] ..... A01H 5/00
(52) U.S. Cl. ..... Plt./107
(58) Field of Search ..... Plt./107

*Primary Examiner*—Anne Marie Grunberg
*Assistant Examiner*—Annette H Para
(74) *Attorney, Agent, or Firm*—Burns, Doane, Swecker & Mathis, LLP

(57) ABSTRACT

A new and distinct variety of landscape shrub rose plant is provided which forms on a continuous basis in clusters attractive double fragrant coral maturing to mauve-pink blossoms. The plant exhibits a compact, upright and bushy growth habit, satiny medium to dark green foliage, and excellent tolerance to Black Spot and Powdery Mildew. The attractive medium to dark green glossy foliage contrasts nicely with the blossom coloration. A tough rose plant of good hardiness is provided. The plant can be grown to advantage as a specimen, border planting, or as a mass planting.

1 Drawing Sheet

Botanical commercial classification: *Rosa hybrida*/Shrub Rose Plant.
Varietal denomination: cv. 'BAIsist'.

SUMMARY OF THE INVENTION

The new variety of *Rosa hybrida* landscape shrub rose plant was created at Yamhill, Oreg. during 1993 by artificial pollination wherein two parents were crossed which previously had been studied in the hope that they would contribute the desired characteristics. The female parent (i.e., the seed parent) was an unnamed seedling designated 4-43A (non-patented in the United States). Such female parent was an unreleased plant from our breeding program that is not available to the public. The male parent (i.e., the pollen parent) was the 'Lillian Gibson' variety (non-patented in the United States). The parentage of the new variety can be summarized as follows:

4-43A×'Lillian Gibson'.

The seeds resulting from the above pollination were sown and plants were obtained which were physically and biologically different from each other. Selective study resulted in the identification during 1996 of a single plant of the new variety having the distinctive ornamental characteristics hereafter described.

It was found that the new variety of the present invention:

(a) exhibits a compact, upright and bushy growth habit,
(b) forms continuously in clusters attractive double fragrant coral maturing to mauve-pink blossoms,
(c) forms satiny medium to dark green adult foliage,
(d) displays excellent tolerance to Black Spot and Powdery Mildew; and
(e) is particularly well suited for growing as attractive ornamentation in parks and gardens.

The blossoms assume a mauve pink or salmon coloration with maturity that contrasts nicely with the medium to dark green satiny foliage. The official American Rose Society blossom color is medium pink. A tough shrub rose plant having good hardiness is provided.

The new variety well meets the needs of the horticultural industry. It can be grown to advantage anywhere in the landscape where attractive ornamentation is desired. The distinctive blossoms commonly are displayed throughout the summer on a continuous basis. The plant can be grown as a specimen, border planting, or as a mass ground cover.

The new variety can be readily distinguished from other varieties including its parental varieties. More specifically, the 4-43A plant forms deep pink opening flowers changing to medium pink having approximately 2.5 petals with light green glossy foliage and assumes a greater height of approximately 1.25 m, and the 'Lillian Gibson' variety forms somewhat smaller double rose-pink blossoms having approximately 40 petals on average. The 'Aunt Honey' variety (non-patented in the United States) forms ovoid buds, the opening flowers are deep pink changing to medium pink having approximately 38 petals, and the plant commonly assumes a greater height of approximately 1.25 m. The 'Rosaweg' variety forms pointed buds, the semi-double opening flowers are medium pink changing to light pink, and the plant commonly assumes a lesser height of approximately 80 cm.

The new variety has been found to undergo asexual propagation by budding on an understock beginning in April 1994, and by the rooting of cuttings. 'Dr. Huey' rootstock was used during the budding. Such asexual propagation by these techniques at Yamhill, Oreg., and at Phoenix, Ariz. has shown that the characteristics of the new variety are stable and are strictly transmissible by such asexual propagation from one generation to another. The new variety grows well on its own roots.

Initially the new plant was designated 93A153-2P. The new variety subsequently has been named the 'BAIsist' variety, and currently is being marketed while using the GARDEN ART and SALMON IMPRESSIONIST trademarks.

BRIEF DESCRIPTION OF THE PHOTOGRAPHS

The accompanying photographs show as nearly true as it is reasonably possible to make the same in color illustrations of this character, typical specimens of the new variety. The rose plants of the new variety had been propagated by the rooting of cuttings, were approximately two and three years of age, and were being grown outdoors at Yamhill, Oreg. during the 2003 season.

DETAILED DESCRIPTION

Figure 1:
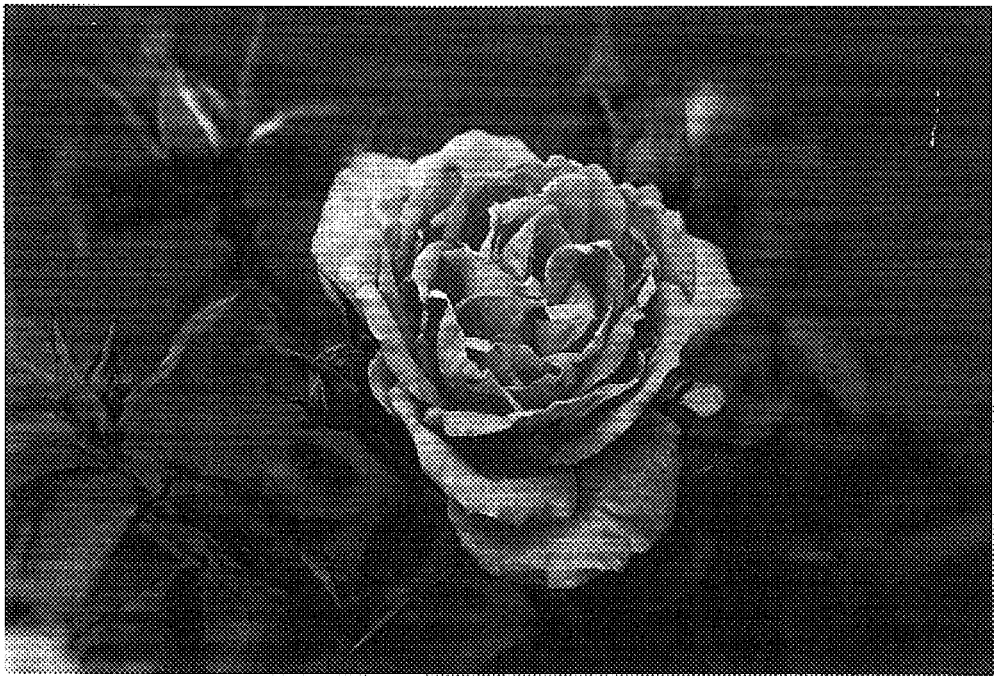
FIG. 1 illustrates typical mature mauve-pink blossom with foliage and buds.
Figure 2:
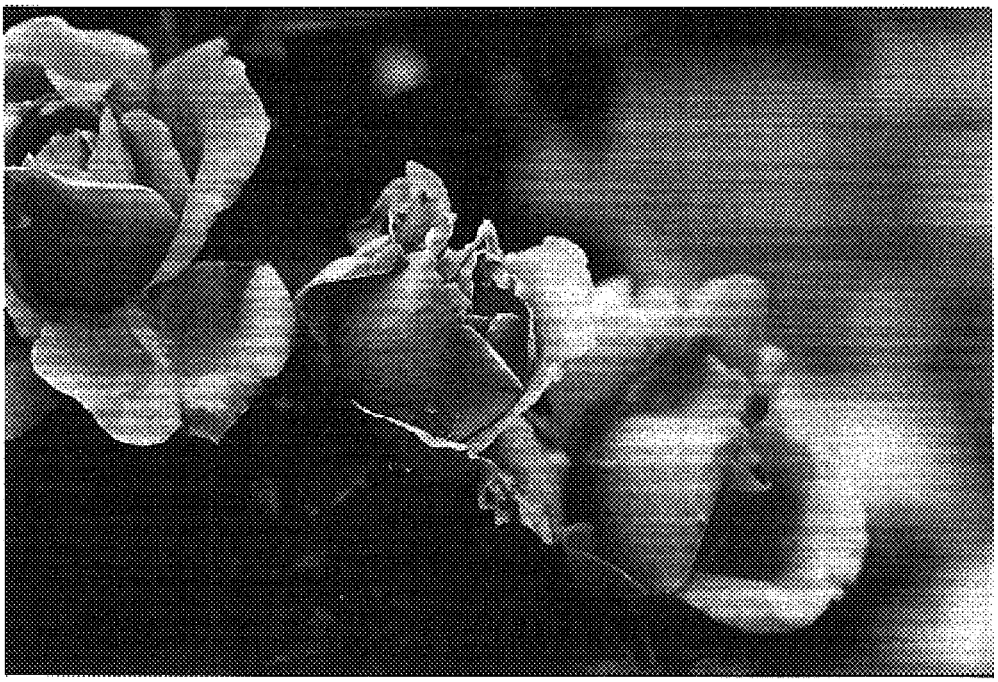
FIG. 2 illustrates a view of three opening blossoms of the new variety.

The chart used in the identification of the colors is that of The Royal Horticultural Society (R.H.S. Colour Chart). Common color terms are to be accorded their ordinary dictionary significance. The description is based on the observation of two and three year-old plants while grown outdoors on their own roots during June and July 2003 at St. Paul, Minn., and Yamhill, Oreg.

Botanical classification: *Rosa hybrida,* var. 'BAIsist'.
Class: Landscape Shrub.
Plant:
- *Height.*—Approximately 90 cm on average at the end of the growing season.
- *Width.*—Approximately 60 to 75 cm on average at the end of the growing season.
- *Habit.*—Compact, dense, upright, and bushy.

Branches:
- *Color.*—Young stems: Yellow-Green Group 144B suffused with Red-Purple Group 59A. Adult wood: Yellow-Green Group 144A.
- *Thorns.*—Size: commonly approximately 0.25 to 0.75 cm in length on average. Color: Red-Purple Group 59B.

Leaves:
- *Stipules.*—Generally parallel with the auricle facing outward.
- *Petioles.*—Upper surface: Yellow-Green Group 144B suffused with Red-Purple Group 59B. Under surface: Yellow-Green Group 144B.
- *Leaflets.*—Number: 3, 5 (most often), and 7. Shape: ovate with a rounded base and an acuminate tip. Margin: serrulate. Texture: bears a satiny finish and is physically firm. General appearance: medium to dark green with a satiny surface when mature. Color (young foliage): Upper surface: Yellow-Green Group 146B suffused with Greyed-Purple Group 187B. Under surface: Yellow-Green Group 146B suffused with Greyed-Purple Group 187B. Color (adult foliage): Upper surface: Yellow-Green Group 147B. Under surface: Green Group 146A and 146B.

Inflorescence:
- *Number of flowers.*—Commonly approximately 8 blooms on average per cluster on a lateral stem.
- *Peduncle.*—Yellow-Green Group 144A and 144B with highlights of Greyed-Purple Group 184B in coloration, and the length is approximately 1.0 cm on average.
- *Sepals.*—Upper surface: Yellow-Green Group 143B with highlights of Greyed-Purple Group 185B with some pubescence. Under surface: Yellow-Green Group 143B with highlights of Greyed-Purple Group 184A. Size: approximately 3.0 cm in length on average with a few foliaceous extensions.
- *Buds.*—Shape: generally rounded. Size: medium. Length: approximately 2.0 cm on average. Diameter: approximately 1.5 cm on average. Color: Upper petal surface: Red Group 39A. Under petal surface: Red Group 39B.
- *Flower.*—Shape: double, and resembles somewhat that of a Tea Rose. Diameter: approximately 9.0 cm on average. Color (when opening begins): Upper surface: Red Group 48A. Under surface: Red Group 48B. Color (when blooming): Upper surface: Between Red Group 51B and Red Group 52D. Under surface: Red Group 51C suffused with Red Group 50B. Color (at end of blooming): Upper surface: Red Group 54B. Under surface: Red Group 55C. Color (basal petal spot): Yellow-Green Group 147C. Fragrance: medium rose. Lasting quality: the blossoms commonly last approximately 4 to 6 days on average on the plant depending upon the temperature and sunlight exposure, and approximately 4 to 5 days in a vase if cut when buds are opening. Petal number: approximately 55 on average under normal growing conditions. Petal shape: generally wedge-shaped with a curled apex. Petal drop: commonly the petals detach cleanly at full blossom maturity. Filament number: commonly approximately 76 on average. Filament color: Yellow-Orange Group 17C. Pistils: approximately 67 on average. Stigmas: Yellow Group 8B in coloration. Styles: Red Group 47B in coloration. Receptacle: separate and free with achenes on the bottom and center. Hips: none available for observation.

Development:
- *Vegetation.*—Vigorous, and compact.
- *Blooming.*—In abundance in June and continuous thereafter.
- *Resistance to diseases.*—Excellent tolerance to Black Spot, and Powdery Mildew.
- *Hardiness zone.*—U.S.D.A. Hardiness Zone Nos. 5 to 9.

We claim:

1. A new and distinct variety of landscape shrub rose plant characterized by the following combination of characteristics:

(a) exhibits a compact, upright and bushy growth habit,
(b) forms continuously in clusters attractive double fragrant coral maturing to mauve-pink blossoms,
(c) forms satiny medium to dark green adult foliage,
(d) displays excellent tolerance to Black Spot and Powdery Mildew; and
(e) is particularly well suited for growing as attractive ornamentation in parks and gardens;

substantially as herein shown and described.

* * * * *